(12) United States Patent
Sjoquist et al.

(10) Patent No.: US 11,324,960 B2
(45) Date of Patent: May 10, 2022

(54) PERMISSION-BASED CONTROL OF INTERFACING COMPONENTS WITH A MEDICAL DEVICE

(71) Applicant: West Affum Holdings Corp., Grand Cayman (KY)

(72) Inventors: Steven E. Sjoquist, Lynnwood, WA (US); David P. Finch, Bothell, WA (US); Erick M. Roane, Kirkland, WA (US); Zoie R. Engman, Kirkland, WA (US); Jonathan P. Niegowski, Issaquah, WA (US); Dusan Beblavy, Bidovce (SK); Martin Pribula, Kosice (SK); Peter Curila, Kosice (SK); Martin Kolesár, Spisska Nova Ves (SK)

(73) Assignee: West Affum Holdings Corp., Grand Cayman (KY)

( * ) Notice: Subject to any disclaimer, the term of this patent is extended or adjusted under 35 U.S.C. 154(b) by 191 days.

(21) Appl. No.: 16/396,628

(22) Filed: Apr. 26, 2019

(65) Prior Publication Data
US 2019/0329056 A1    Oct. 31, 2019

Related U.S. Application Data

(60) Provisional application No. 62/663,131, filed on Apr. 26, 2018.

(51) Int. Cl.
*H04L 9/32* (2006.01)
*H04L 9/40* (2022.01)
(Continued)

(52) U.S. Cl.
CPC ........ *A61N 1/3904* (2017.08); *A61B 5/02438* (2013.01); *A61N 1/046* (2013.01);
(Continued)

(58) Field of Classification Search
CPC .... A61N 1/3904; A61N 1/046; A61N 1/0484; A61N 1/3987; A61N 1/3993;
(Continued)

(56) References Cited

U.S. PATENT DOCUMENTS

| 3,724,355 A | 4/1973 | Unger |
| 4,583,524 A | 4/1986 | Hutchins |

(Continued)

FOREIGN PATENT DOCUMENTS

| DE | 2005060985 A2 | 6/2007 |
| EP | 2305110 A1 | 4/2011 |

(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Jounal, May 31, 2013, pp. 1-14, doi:10.1093/eurheartj/eht167, European Society of Cardiology.

(Continued)

*Primary Examiner* — Michael S McNally
(74) *Attorney, Agent, or Firm* — Christensen O'Connor Johnson Kindness PLLC (57) ABSTRACT

Disclosed are embodiments directed to security methods applied to connections between components in a distributed (networked) system including medical and non-medical devices, providing secure authentication, authorization, patient and device data transfer, and patient data association and privacy for components of the system.

9 Claims, 8 Drawing Sheets

(51) Int. Cl.
  *A61N 1/39* (2006.01)
  *A61B 5/024* (2006.01)
  *A61N 1/04* (2006.01)
  *G06F 21/33* (2013.01)
  *H04L 29/06* (2006.01)
  *A61B 5/00* (2006.01)
  *A61N 1/372* (2006.01)
  *A61B 5/361* (2021.01)
  *A61B 5/363* (2021.01)

(52) U.S. Cl.
  CPC ......... *A61N 1/0484* (2013.01); *A61N 1/3987* (2013.01); *A61N 1/3993* (2013.01); *G06F 21/33* (2013.01); *H04L 9/3268* (2013.01); *H04L 63/0823* (2013.01); *A61B 5/361* (2021.01); *A61B 5/363* (2021.01); *A61B 5/6805* (2013.01); *A61B 5/74* (2013.01); *A61N 1/37258* (2013.01); *A61N 1/3925* (2013.01)

(58) Field of Classification Search
  CPC .............. A61N 1/37258; A61N 1/3925; A61B 5/02438; A61B 5/361; A61B 5/363; A61B 5/6805; A61B 5/74; G06F 21/33; H04L 9/3268; H04L 63/0823
  USPC .......................................................... 713/156
  See application file for complete search history.

(56) References Cited

U.S. PATENT DOCUMENTS

| | | |
|---|---|---|
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lysler |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,450,942 B1 | 9/2002 | Lapanashvili et al. |
| 6,463,535 B1* | 10/2002 | Drews .................. G06F 9/4416 713/176 |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 10/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2004/0171374 A1* | 9/2004 | Little ...................... H04L 29/06 455/418 |
| 2005/0107833 A1 | 5/2005 | Freeman et al. |
| 2005/0107834 A1 | 5/2005 | Freeman et al. |
| 2005/0268098 A1* | 12/2005 | Oh .......................... G06F 21/10 713/168 |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0212381 A1* | 8/2013 | Bousamra ........... H04L 63/0823 713/156 |
| 2013/0231711 A1 | 9/2013 | Kaib |

(56) References Cited

U.S. PATENT DOCUMENTS

| | | |
|---|---|---|
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buritonil et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2016/0287470 A1 | 10/2016 | Lewis et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0279612 A1* | 9/2017 | Liang ................. H04L 9/30 |
| 2017/0319862 A1 | 11/2017 | Foshee, Jr. et al. |
| 2017/0367591 A1 | 12/2017 | Jorgensen |
| 2018/0001083 A9 | 1/2018 | Finch et al. |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0221645 A1 | 8/2018 | Medema et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0060644 A1 | 2/2019 | Finch et al. |
| 2019/0076666 A1 | 3/2019 | Medema |
| 2019/0116896 A1 | 4/2019 | Armour et al. |
| 2019/0265938 A1* | 8/2019 | Kim ................. G06F 3/04817 |
| 2019/0321650 A1 | 10/2019 | Raymond et al. |

FOREIGN PATENT DOCUMENTS

| | | | |
|---|---|---|---|
| JP | 4320257 | A | 3/2005 |
| JP | 5963767 | A | 1/2014 |
| JP | 2014526282 | A | 10/2014 |
| WO | 98/39061 | A2 | 9/1998 |
| WO | 1998039061 | A2 | 9/1998 |
| WO | 2011/146448 | A1 | 11/2011 |
| WO | 2012/064604 | A1 | 5/2012 |
| WO | 2012064604 | A1 | 5/2012 |
| WO | 2012/151160 | A1 | 11/2012 |
| WO | 2015/056262 | A1 | 4/2015 |

OTHER PUBLICATIONS

LIFECOR LifeVest System Model WCD 3100 Operator's Manual, 2006, PN 20B0040 Rev FI, Zoll Lifecor Corporation, Pittsburgh, PA.

Heartstart MRx and XL AED Algorithm—Application Note, Jul. 2001, Edition 2 Phillips Healthcare, USA.

ZOLL LifeVest Model 4000 Patient Manual PN 20B0047 Rev B, (C) 2009-2012.

Heartstart MRx and XL AED Algorithm—Application Note, Jul. 2001, Edition 2 Philips Healthcare, USA.

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

| Subject | Identity of the Certificate Holder |
|---|---|
| Issuer | Identity of Certifying Authority |
| Expiration | Date after which digital certificate is no longer valid |
| Public Key | Public Key of the Certificate Holder |
| Algorithm | Hashing algorithm used to sign the digital certificate |
| Unique Identifier | Value that uniquely identifies the digital certificate |

| Permissions | Tasks that Certificate Holder is authorized to perform |
|---|---|
| Other data | Arbitrary or structured data that may be verified or trusted |

| Signature | Signature of the Certifying Authority created using Certifying Authority's private key |
|---|---|

Security Certificate

CERT CREATION

Fig. 7

CERT USE

Fig. 8

PERMISSION-BASED CONTROL OF INTERFACING COMPONENTS WITH A MEDICAL DEVICE

CROSS REFERENCE TO RELATED APPLICATIONS

This patent application claims the benefit of and priority to U.S. Provisional Patent Application Ser. No. 62/663,131, filed on Apr. 26, 2018, titled "System And Method For Permission-Based Control Of Interfacing Components With A Medical Device," the disclosure of which is hereby incorporated by reference for all purposes.

SUMMARY OF THE DISCLOSURE WITH BACKGROUND INFORMATION

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Medical device technology has evolved and advanced along with most other areas. Medical devices are often now as interconnected as any other technology, such as conventional computing devices and telephone systems. For that reason, medical devices routinely gather, collect, and store patient data.

Frequently, a medical device, such as a Wearable Cardioverter Defibrillator (WCD) may interface with other components, sometimes many other components, for the purpose of providing therapy to a patient. In connection with that therapy, the WCD may initiate or receive requests to initiate communication sessions with other medical devices or other non-medical devices. To ensure that private patient data is not compromised, and to ensure the integrity of the operation of critical life-saving medical devices, the WCD should only allow communication sessions with authorized and/or approved components.

Embodiments of the disclosure implement a platform to enable secure communication between medical devices and non-medical devices that also ensures only trusted components are allowed to communicate with a medical device, especially a medical device that provides critical life-saving therapy. In various embodiments, the communication platform is implemented using at least a security certificate that is attested to by a trusted Certificate Authority. The security certificate is used to authenticate trusted components to each other, and to enable secure (encrypted) communication between such trusted components.

In another aspect, embodiments build on the secure communication platform to ensure that only authorized users have access to patient data. In such embodiments, the secure communication platform includes a patient unique identifier (UID) that is used, in connection with the security certificates, to ensure that only trusted components with authorized access to a patient's data are provided access to the patient's data.

DETAILED DESCRIPTION

Generally described, embodiments are directed to security methods applied to connections between components in a distributed (networked) system including medical and non-medical devices, providing secure authentication, authorization, patient and device data transfer, and patient data association and privacy for components of the system.

Various embodiments are described more fully below with reference to the accompanying drawings, which form a part hereof, and which show specific exemplary implementations for practicing various embodiments. However, other embodiments may be implemented in many different forms and should not be construed as limited to the embodiments set forth herein; rather, these embodiments are provided so that this disclosure will satisfy formal statutory requirements. Embodiments may be practiced as methods, systems or devices. Accordingly, embodiments may take the form of a hardware implementation, an entirely software implementation, or an implementation combining software and hardware aspects. The following detailed description is, therefore, not to be taken in a limiting sense.

The logical operations of the various embodiments are implemented (1) as a sequence of computer implemented steps running on a computing system and/or (2) as interconnected machine modules within the computing system. The implementation is a matter of choice dependent on various considerations, such as performance requirements of the computing system implementing the embodiment. Accordingly, the logical operations making up the embodiments described herein may be referred to alternatively as operations, steps or modules.

Illustrative Environment and Systems

Figure 1:
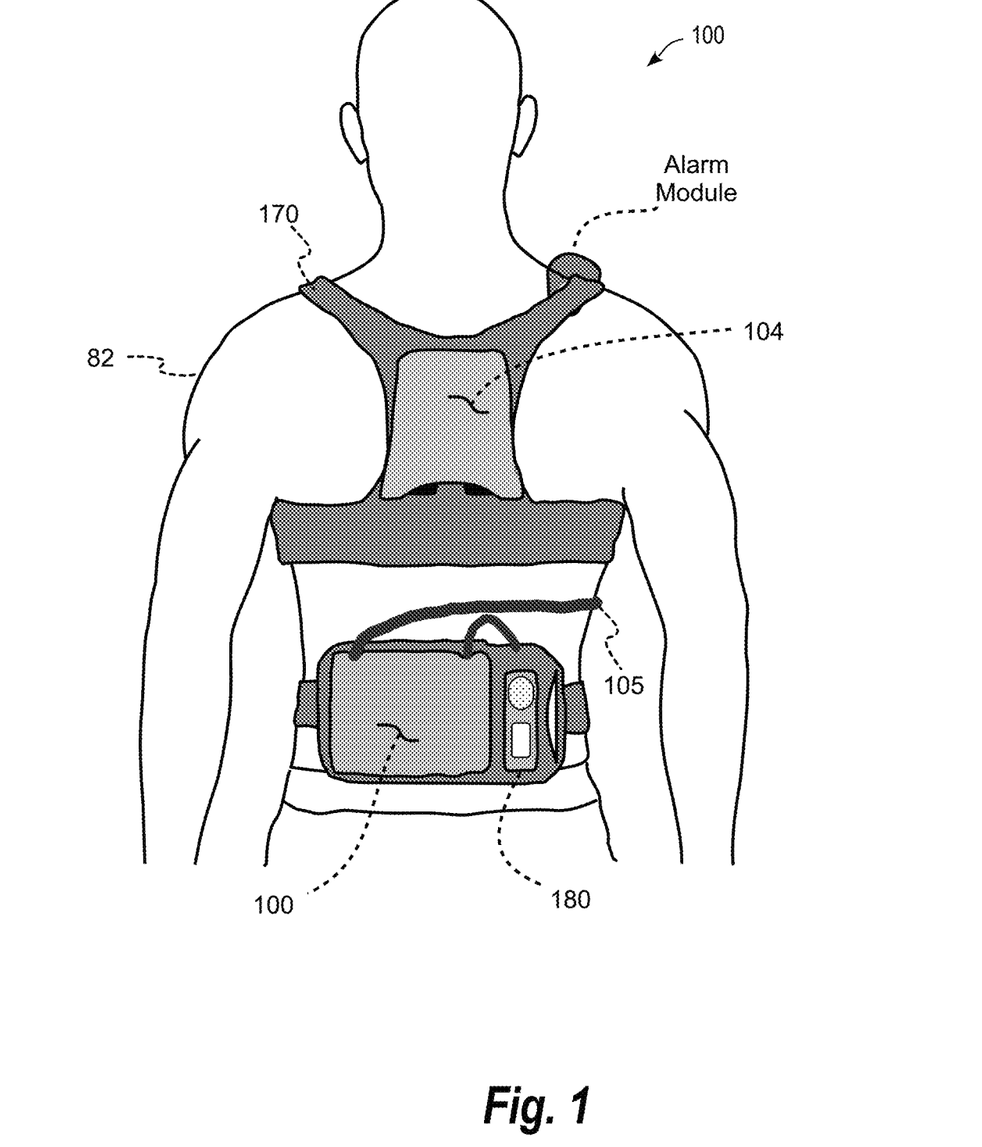
FIG. 1 is a conceptual diagram of a wearable cardioverter defibrillator system made in accordance with an embodiment of this disclosure.

FIG. 1 is a conceptual diagram generally showing components of a medical device that may be adapted to implement embodiments of this disclosure. In this particular example, the medical device is a wearable cardioverter defibrillator (WCD) system.

A patient 82, who is ambulatory, is shown in FIG. 1. Patient 82 may also be referred to as "wearer," since the patient wears at least some components of the WCD System 100. One component of the WCD System 100 is a garment 170 that is wearable by patient 82. The garment 170 acts as a support structure for several of the other components of the WCD System 100. The garment 170 is a semi-rigid wearable element sufficient to support and contain at least some other components of the WCD System 100. The illustration shown in FIG. 1 is provided merely to describe concepts about the garment 170, and is not to be construed as limiting how garment 170 may be implemented in various embodiments, or how it is worn.

Indeed, garment 170 can be implemented in many different ways. For example, it may be implemented as a single component or as a combination of multiple components. In some embodiments, garment 170 includes a harness, one or more belts or straps, etc. In such embodiments, those items can be worn around the torso or hips, over the shoulder, or the like. In other embodiments, garment 170 includes a container or housing, which may be waterproof.

As shown in FIG. 1, the WCD System 100 includes an external defibrillator 101, defibrillation electrodes 104, and electrode leads 105 which couple the defibrillator 101 to the defibrillation electrodes 104. In many embodiments, defibrillator 101 and defibrillation electrodes 104 are supported by garment 170. In other embodiments, defibrillator 101 may be supported by an ancillary article of clothing, such as the patient's belt.

The WCD System 100 may also include a monitoring device (e.g., monitor 180) to monitor the patient 82, the patient's environment, or both. In many embodiments, the monitor 180 is coupled to one or more sensors, such as electrocardiogram electrodes. Using those sensors, the monitor 180 detects criteria upon which a shock/no-shock decision can be made.

In certain embodiments, monitor 180 is implemented as a component of the defibrillator 101. In other embodiments, monitor 180 may be implemented as a stand-alone monitoring device supported by the garment 170 or perhaps worn separately, such as on the patient's wrist or belt. In such cases, monitor 180 may be communicatively coupled with other components, which are coupled to garment 170. Such communication can be implemented by a communication module, as will be described below.

Optionally, the WCD System 100 may include a fluid that can be deployed between the defibrillation electrodes and the patient's skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes and sensing electrodes.

The WCD System 100 is configured to defibrillate the patient 82 by delivering an electrical shock (sometimes referred to as a pulse, defibrillation shock, therapy, or therapy shock) to the patient's heart through the patient's body. When defibrillation electrodes 104 make good electrical contact with the body of patient 82, defibrillator 101 can administer, via electrodes 104 a brief, strong electric shock through the patient's body. The shock is intended to go through and restart the patient's heart, in an effort to save the life of the patient 82.

Various embodiments may also provide remote sensors, such as ECG electrodes, which are in operative communication with the defibrillator 101. The remote sensors provide the defibrillator 101 with physiological information upon which the shock/no-shock decision can be made. In further accordance with this disclosure, these remote sensors are either separate or separable from the garment 170.

In various embodiments, and as discussed in greater detail below, the WCD System 100 illustrated in FIG. 1 may also communicate with other components using a secure communication platform.

Figure 2:
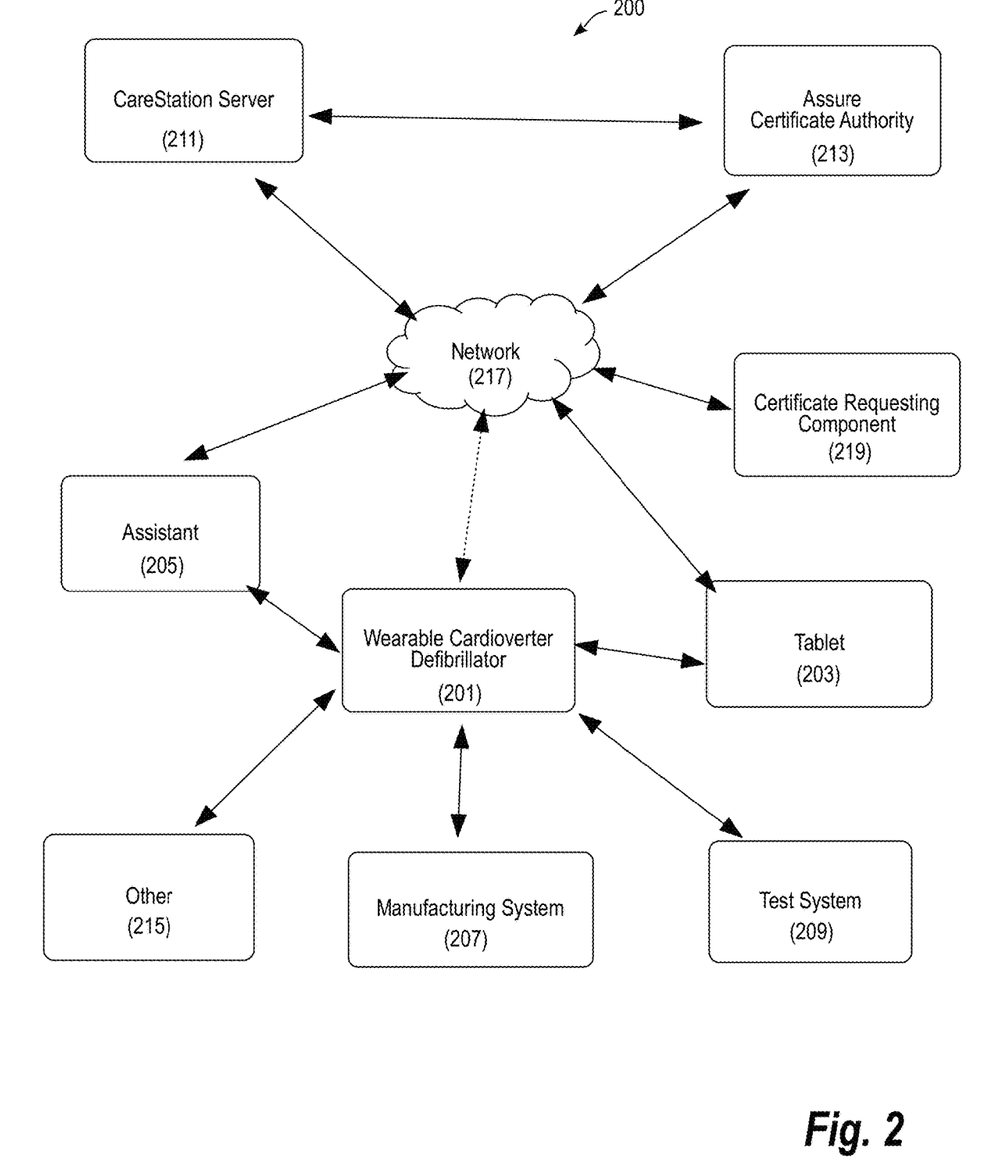
FIG. 2 is a conceptual block diagram generally illustrating components of a WCD system in which embodiments of the disclosure may be implemented.

FIG. 2 is a conceptual block diagram generally illustrating components of a WCD system 200 in which embodiments of the disclosure may be implemented. Illustrated is a distributed WCD system 200 that contains multiple components, both medical and non-medical devices, that communicate with each other using various communication means. These communication means may include known network communication technologies such as Bluetooth, Wi-Fi, USB, Cellular Data, Near Field Communication (NFC), and Ethernet. In addition, the communication means may implement known networking protocols such as HTTP and Internet protocols.

Shown in FIG. 2 are major elements of the illustrative WCD system 200 with examples of network technologies they may use to communicate with each other. Certain of the components may be referred to using terms like "Assure," "Assistant," and "CareStation." Those terms are merely a naming convention for simplicity of discussion and are not intended to, nor do they in fact, refer to any particular technologies which may bear the same or similar names just because they bear the same names.

In various embodiments, an aspect of system connection and interaction is that certain elements must allow only connection to and communication with other trusted other elements. Some embodiments, for example, are implemented using a Wearable Cardioverter Defibrillator (WCD) device, which can analyze an ECG of patients wearing the WCD device and deliver defibrillation therapy if necessary. It is important that connection and communications are only allowed from trusted elements.

Some embodiments are configured to ensure only authorized elements can connect and communicate with other elements using secure certificates issued by a private Assure certificate authority. A security certificate is an encrypted electronic record that contains information about the element requesting connection and is signed by an external and trusted Certificate Authority. Each of the illustrative components will be generally described here.

Figure 3:
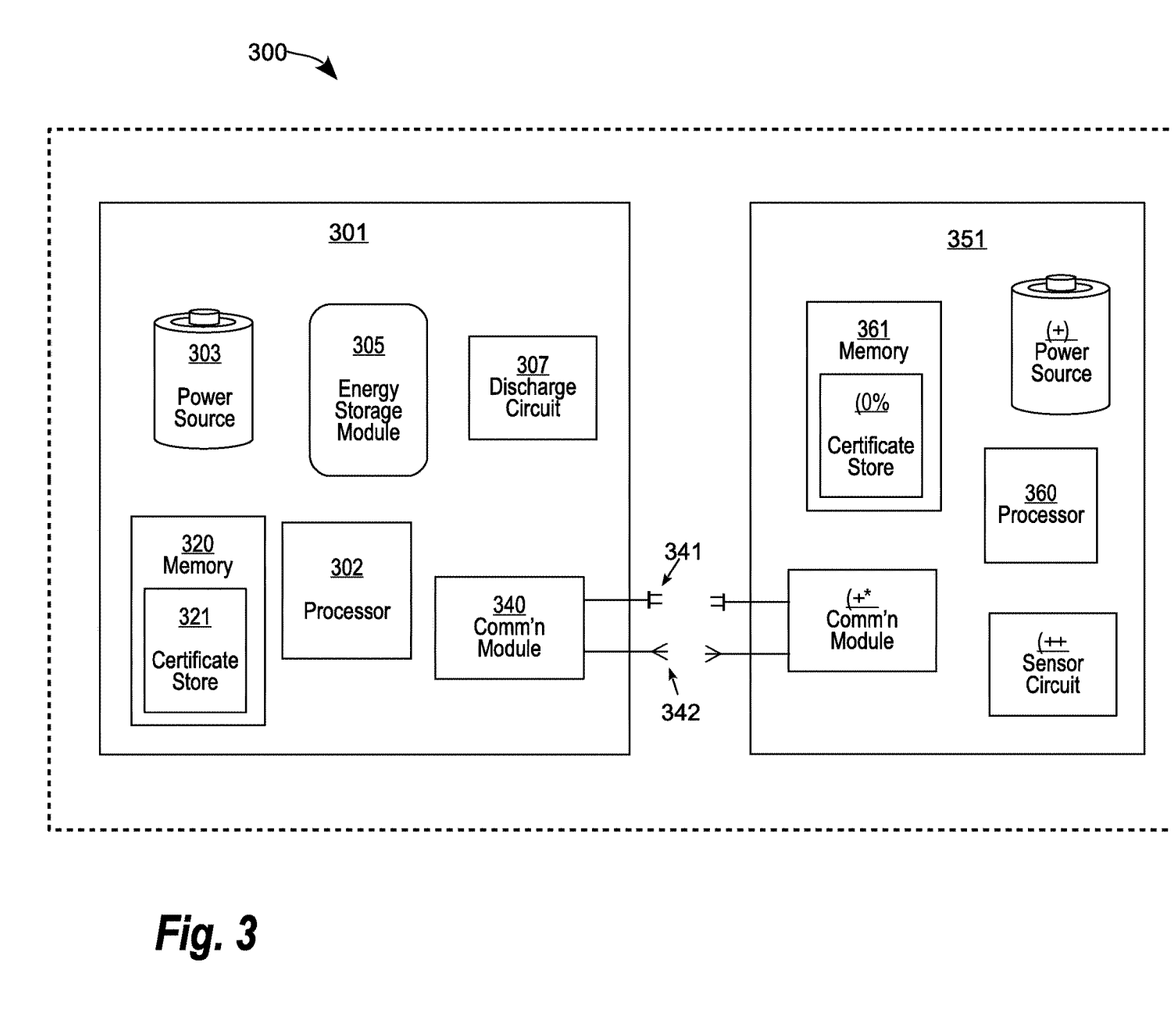
FIG. 3 illustrates functional components of one illustrative WCD system implemented in accordance with the teachings of this disclosure.

The WCD system 200 includes a Wearable Cardioverter Defibrillator (WCD) 201, which is typically considered a medical device. The WCD 201 is a medical device configured to deliver a shock therapy to a patient in response to a cardiac event, such as a ventricular fibrillation. The WCD 201 is able to accept connections from other components and allow them to transfer data or perform critical operations on the WCD 201. One specific example of a WCD 201 is illustrated in FIG. 3 and described below.

A Tablet 203 is a mobile device that, in the preferred embodiment, allows clinicians to view WCD status information and to configure the WCD 201. In the preferred embodiment, the Tablet 203 is considered a medical device although in other embodiments it may not be.

An Assistant 205 is a mobile device that mirrors some aspects of WCD status and transfers patient and device data to a CareStation Server 211. The Assistant 205 is considered a medical device in the preferred embodiment, although in other embodiments it may not be.

Manufacturing System 207 is a system for testing and configuring the WCD 201 in a manufacturing environment. The manufacturing system 207 is not generally considered a medical device.

A Test System 209 is a system for verification of certain functionality of the WCD 201. The Test System 209 is not generally considered a medical device, although in other embodiments it may be.

A CareStation Server 211 is a cloud-based system for receiving and storing device and patient data, and accepts patient and device data transmissions from other elements of the system. Clinical and support personnel can view the data stored at the CareStation Server 211. In various embodiments, the CareStation Server 211 also provides access to security certificate services such as Certificate Signing Requests (CSRs) and a certificate revocation list. Generally, the CareStation Server 211 is considered a medical device.

An Assure Certificate Authority 213 is a system that provides security certificate services such as issuing Assure root certificates and performing certificate signing on CSRs. In the preferred embodiment, the Assure Certificate Authority 213 is not generally considered a medical device.

A certificate requesting component 219 is included that is configured to request a security certificate (described below) on behalf of another component that seeks to be trusted by other components in the WCD system 200, such as the WCD 201. Generally stated, the certificate requesting component 219 is programmed to generate a public/private key pair and a Certificate Signing Request (CSR) on behalf of another component. Alternatively, the certificate requesting component 219 may obtain only the public key portion of the public/private key from the other component. The certificate requesting component 219 is itself already trusted within the WCD system 200. The certificate requesting component 219 is not generally considered a medical device, but its functionality may be incorporated into a medical device.

Other components 215 may also be included in the WCD system 200 that interface with the WCD 201 and use security certificates to connect with the WCD 201 and perform various operations with it. The other components 215 may or may not be considered medical devices.

Figure 4:
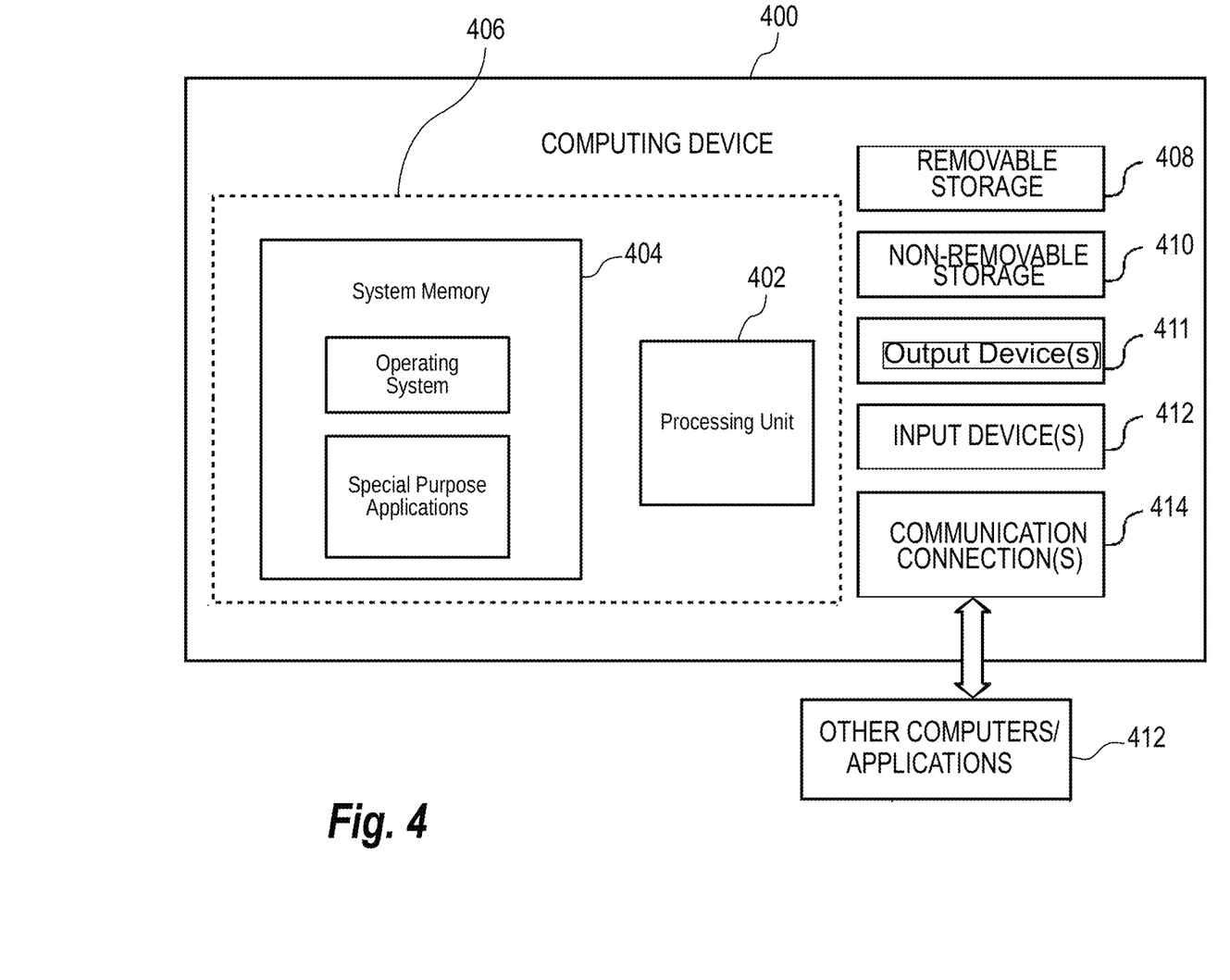
FIG. 4 is a functional block diagram of an exemplary computing device that may be used to implement components of one or more embodiments.

Several of the components of the WCD system 200 may be implemented with computing devices. One illustrative computing device which may be used to implement various components is illustrated in FIG. 4 and described below.

Each of the several components of the WCD system 200 communicate with the WCD 201 and with each other using various communication means. Various components, such as the Tablet 203 and the Test System 209, for example, may communicate directly with the WCD 201, such as by connecting directly to the WCD 201 either wirelessly or with a wired connection. Other components, such as the CareStation Server 211, may connect to the WCD 201 indirectly, such as over a network connection 217.

In accordance with the disclosure, the various components of the WCD system 200 communicate with each other and with the WCD 201 using security certificates to ensure trusted communications. The security certificates and trusted communications are described in detail below.

FIG. 3 illustrates functional components of one illustrative WCD system 300 implemented in accordance with the teachings of this disclosure. Generally stated, the core operative components of the WCD system include a defibrillator 301 and a trusted component 351. Each of those components will now be described, followed by a brief overview of the operation of the WCD system.

The defibrillator 301 of the illustrative WCD includes at least a processor, a power source, an energy storage module, and a discharge circuit. The processor 302 may be implemented as a digital and/or analog processor, such as microprocessors and Digital Signal Processors (DSPs); microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 302 may include, or have access to, a memory 320 that may be either volatile, nonvolatile, or some combination of the two. Computer executable instructions may be stored in the memory 320. The instructions generally provide functionality by defining methods as may be disclosed herein or understood by one skilled in the art in view of this disclosure. The memory may be implemented as Read-Only Memory (ROM), Random Access Memory (RAM), magnetic disk storage media, optical storage media, flash memory, any combination of these, or the like.

Figure 5:
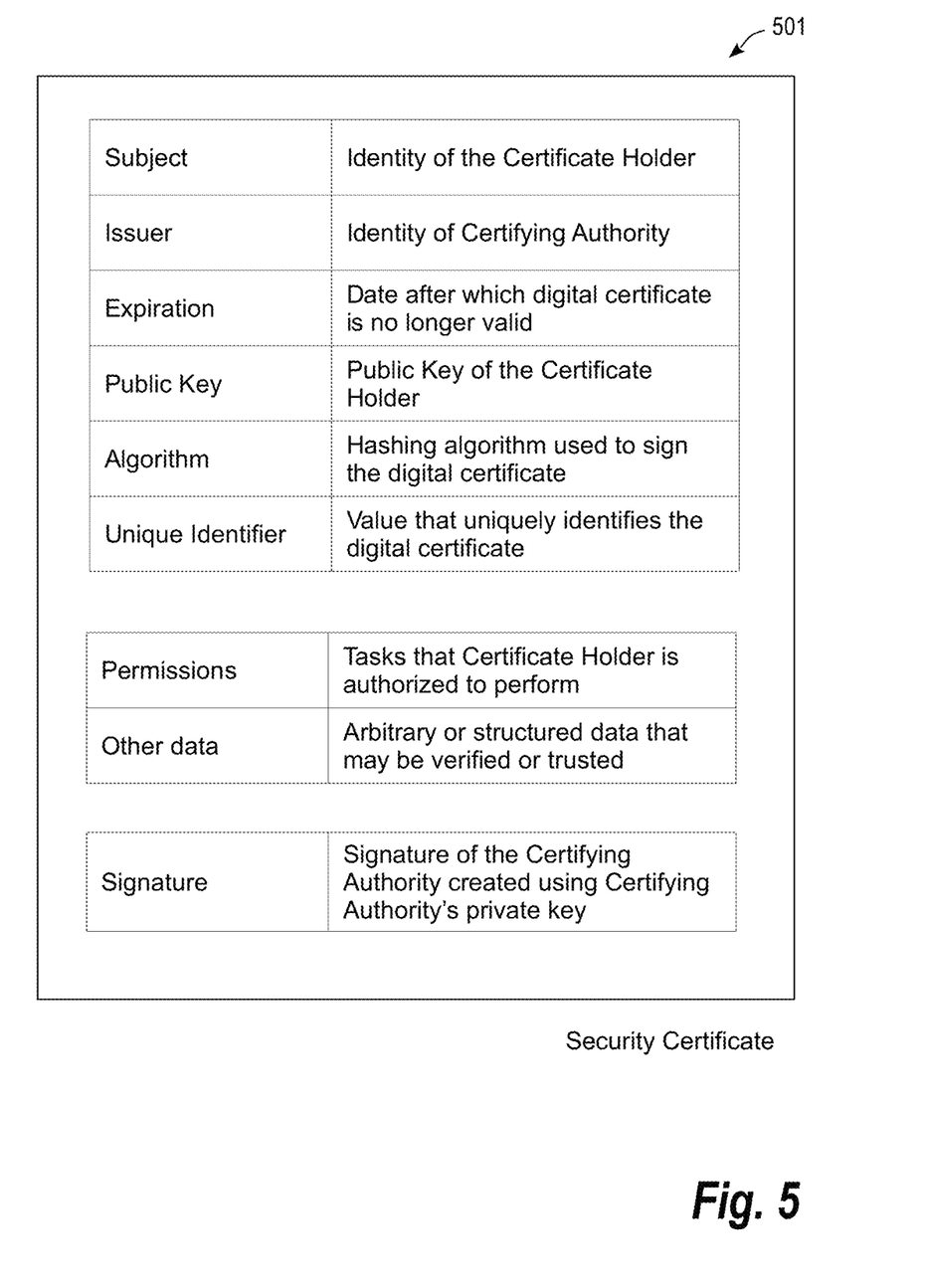
FIG. 5 is a conceptual diagram of a security certificate (also referred to as a digital certificate) that may be used in various embodiments of the disclosure.

In accordance with the present disclosure, the memory 320 further includes a certificate store 321. Within the certificate store 321 resides various security certificates (also referred to as digital certificates) which enable secure communication with trusted components. One specific example of an illustrative security certificate is shown in FIG. 5 and described below. Generally stated, the security certificates enable the defibrillator 301 to securely identify a trusted component 351 and may additionally identify specific permissions which the trusted component 351 has.

The power source 303 may be any type of electrical component sufficient to provide power, such as a battery. Other types of power source 303 could include an AC power override, for where AC power will be available, an energy storage capacitor, and so on. Appropriate components may also be included to provide for charging or replacing power source 303.

The defibrillator 301 may additionally include an energy storage module 305. Energy storage module 305 is where electrical energy is stored temporarily in the form of an electrical charge, when preparing it for discharge to administer a shock. Energy storage module 305 can be charged from power source 303 to the desired amount of energy. In typical implementations, module 305 includes a capacitor, which can be a single capacitor or a system of capacitors, and so on. In some embodiments, energy storage module 305 includes a device that exhibits high power density, such as an ultracapacitor.

The defibrillator component also includes a discharge circuit 307. When the processor 302 determines that a shock is appropriate, the processor 302 instructs the discharge circuit 307 to discharge the electrical charge stored in energy storage module 305 to the patient. When so controlled, the discharge circuit 307 causes the energy stored in energy storage module 305 to be discharged to defibrillation electrodes 309, so as to cause a shock to be delivered to the patient.

In accordance with this disclosure, defibrillator 301 also includes a communication module 340 configured to enable communication with remote components. In certain embodiments, communication module 340 includes a wireless communication facility to enable wireless communication between the defibrillator 301 and remote components. Examples of wireless communication that may be enabled include 802.11 (WiFi) communication, Bluetooth communication, Near Field Communication (NFC), infrared communication, or the like.

In other embodiments, communication module 340 includes a wired communication facility to enable wired communication. In such embodiments, defibrillator 301 may include a communication port 341 through which the wired communication may be effected. Examples of such wired communication may include a universal serial bus connector (e.g., USB-C, micro-USB, mini-USB, USB-A, or the like), a coaxial connector, an Ethernet connector, a 12-lead connector, or the like.

The communication module 340 enables the defibrillator 301 to communicate with other components, such as trusted component 351. In this way, the processor 302 may receive sensory input data upon which it can base a shock/no-shock decision, it may receive configuration instructions, it may transmit patient or therapy data to other components, or the like.

The trusted component 351 is another component of the WCD system 300. In this example, the trusted component 351 includes a remote processor 260 and a communication module 357. The communication module 357 of the trusted component 351 may function similar to the component of the same name described above (i.e., communication module 340). In other words, the communication module 357 of the trusted component 351 may enable either wired or wireless communication between the trusted component 351 and the defibrillator 301 (or any other component of the WCD system 300).

The remote processor 360 is configured to control and manage the operation of the several components of the trusted component 351 and to facilitate communication between the trusted component 351 and the defibrillator 301. The trusted component 351 may further include a power source 359.

In accordance with the present disclosure, the trusted component 351 further includes a remote memory 361 which further includes a certificate store 362. Within the certificate store 362 resides various security certificates (also referred to as digital certificates) which enable secure communication with trusted components. The trusted component 351 of the preferred embodiment includes its own security certificate which is signed by a Certificate Authority as described below.

In many embodiments, trusted component 351 is in operative communication with the defibrillator 301 for various purposes, such as to configure the defibrillator 301 or to extract device or patient data from the defibrillator 301.

In various embodiments, a sensor circuit 355 may be implemented, such as an ECG electrode, an accelerometer, or the like. However, sensor circuit 355 may alternatively be implemented as one or more of various other sensors.

Embodiments of the trusted component 351 may be implemented in many ways. For instance, trusted component 351 may be implemented as a mobile device (e.g., a specially adapted cellular phone) which the patient may carry in the hand or, perhaps, in a pocket. Alternatively, trusted component 351 may be implemented as a fixed computing device, such as a desktop computer or server.

In operation, the trusted component 351 and the defibrillator 301 communicate with each other using their respective communication modules (i.e., communication module 340 and communication module 357). In accordance with the disclosure, the trusted component 351 transmits to the defibrillator 301 a security certificate that enables the defibrillator 301 to verify the authenticity of the trusted component 351. In addition, the security certificate may also specify particular permissions or tasks that the trusted component 351 is authorized to perform.

FIG. 4 is a functional block diagram of an exemplary computing device 400 that may be used to implement components of one or more embodiments. The computing device 400, in one basic configuration, includes at least a processor 402 and a memory 404. Depending on the exact configuration and type of computing device, memory 404 may be volatile (such as RAM), non-volatile (such as ROM, flash memory, etc.), or some combination of the two. This basic configuration is illustrated in FIG. 4 by dashed line 406.

Memory 404 includes at least an operating system and may additionally include other special purpose components. The operating system includes components and functions to enable the computing device 400 to function at a basic level. Examples of the operating system components may include a file system and graphical user environment. The operating system may also include components for communicating over a local or wide area network, such as an Internet browser. Special purpose components may include other components to enable the computing device 400 to perform specific tasks. For instance, the special purpose components may include a certificate store with security certificates, a certificate signing routine, a hashing algorithm, a certificate revocation list, a facility for creating public and private keys, or the like. In addition, like the operating system, the special purpose components may also include components for communicating over a local or wide area network, such as an Internet browser, or the like.

Computing device 400 may have other features and functionality also. For example, device 400 may also include additional storage (removable and/or non-removable) including, but not limited to, magnetic or optical disks or tape. Such additional storage is illustrated in FIG. 4 by removable storage 408 and non-removable storage 410. Computer storage media includes volatile and nonvolatile, removable and non-removable media implemented in any method or technology for storage of information such as computer readable instructions, data structures, program modules or other data. Memory 404, removable storage 408 and non-removable storage 410 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can accessed by device 400. Any such computer storage media may be part of device 400.

Computing device 400 includes one or more communication connections 414 that allow computing device 400 to communicate with one or more computers and/or applications 413. Device 400 may also have input device(s) 412 such as a keyboard, mouse, digitizer or other touch-input device, voice input device, etc. Output device(s) 411 such as a monitor, speakers, printer, PDA, mobile phone, and other types of digital display devices may also be included. These devices are well known in the art and need not be discussed at length here.

FIG. 5 is a conceptual diagram of a security certificate 501 (also referred to as a digital certificate) that may be used in various embodiments of the disclosure. In certain embodiments, the security certificate 501 is a digital file that includes various fields of data. Those fields may include one or more of a subject, an issuer, an expiration, an algorithm, and a unique identifier. All of these fields need not be included in every embodiment, and other fields may also be included which are not described here. These fields are provided as illustrative only.

The subject field may identify the certificate holder or the entity with whom the security certificate 501 is associated.

The certificate holder may be an individual, an organization, a specific computing device, or any entity whose identity has been verified and whose trust is being attested to by a certifying authority (e.g., Certificate Authority 213).

The issuer field may identify a trusted Certificate Authority who may be trusted to verify the authenticity of entities. In one example, an Assure Certificate Authority may be established and trusted to verify the identity of various components that are authorized to communicate with, for example, a WCD or other components of a WCD system.

An expiration field may identify a date after which the security certificate is no longer valid or can no longer be used to trust the subject. In some embodiments, a "not before" field may also be included to identify a date before which the security certificate is not valid.

A public key portion of the security certificate is included to provide a public key for the subject and related public key information. Public/private key pairs are used in Public Key Infrastructure (PKI) systems to facilitate asymmetric cryptography. The public key information may include further information that describes the public key, such as the algorithm (e.g. Elliptic Curve Public Key), the key size (e.g. 256 bits), and the key usage (e.g. can encrypt, verify, derive). The public key portion of the security certificate 501 enables recipients of the security certificate 501 to communicate securely with the subject through encrypted communication sessions.

An algorithm field may be included in the security certificate 501 to specify a particular algorithm that was used to sign the certificate as described below. Examples of algorithms which may be used include SHA-1, SHA-2, SHA-256, and the like.

A unique identifier or serial number is also included to uniquely identify the security certificate. Note that the unique identifier should be distinguished from the subject in that the subject identifies the trusted entity or the entity with which the security certificate is associated whereas the unique identifier identifies the actual security certificate itself.

Optionally, one or more permissions fields may be included in the security certificate 501. In some embodiments, certain elements of the WCD System (such as the WCD) need to govern what operations other connected components are allowed to perform while in communication. For example, in some embodiments the WCD may be configured to allow a limited set of element types to change critical configuration parameters of the WCD but to prevent other element types from doing so. An example of this may be that the WCD can be configured to allow a Tablet to configure such parameters but it doesn't allow an Assistant to do so. In such embodiments, one or more fields of the security certificate 501 (collectively referred to as the "permissions" field for simplicity of discussion) may include information sufficient to identify what tasks or operations that the certificate holder is authorized to perform with respect to the WCD. That information may take the form of actual enumerated permissions or, more likely, an identification of a class of device in which the certificate holder falls and the class of device may implicitly define the permissions authorized by the certificate holder.

Other data fields may also be included and used for various reasons. Arbitrary or structured data may be included to provide or convey any manner of information deemed worthy of trust or having a need to ensure its integrity.

A signature is also included with the security certificate 501. The signature is a data structure that represents an attestation to the authenticity of the security certificate 501. The signature is created by the issuer (e.g., the Certificate Authority) and is verifiable using a security certificate (or digital certificate) of the issuer. Although the signature may be created in different ways, one example may be that the body 550 of the security certificate is input to the algorithm (e.g., a hashing algorithm) identified within the security certificate together with a private key of the issuer. The algorithm creates a unique value based on the body of the security certificate and the issuer's private key. The issuer's public key can then be used by the identified algorithm to verify that the body of the security certificate has not been changed since the signature was created by the issuer. In this way, the integrity of the data in the body of the security certificate can be trusted so long as the issuer is trusted.

Operation of Preferred Embodiments

Figure 6:
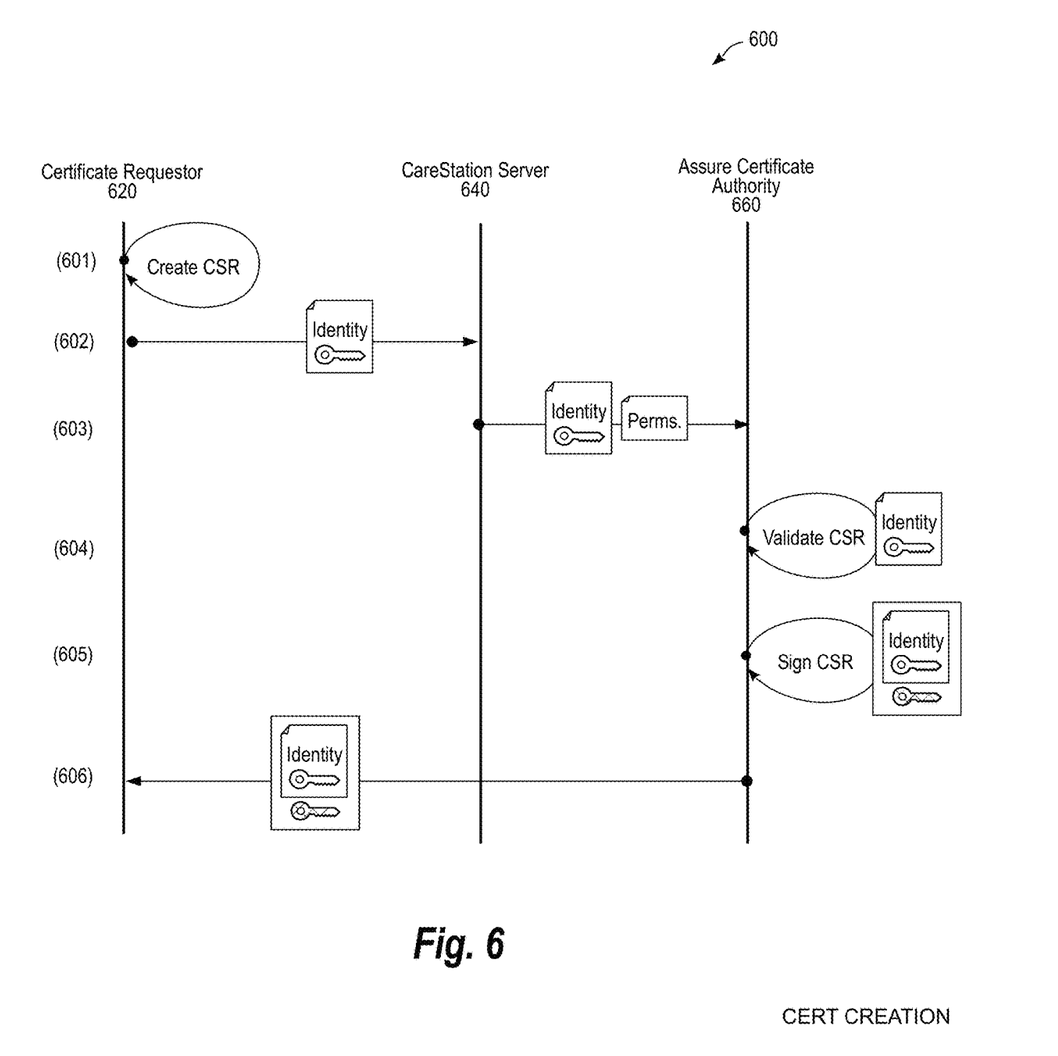
FIG. 6 is a functional flow diagram generally illustrating a process 600 for creation of a security certificate in accordance with this disclosure.
Figure 7:
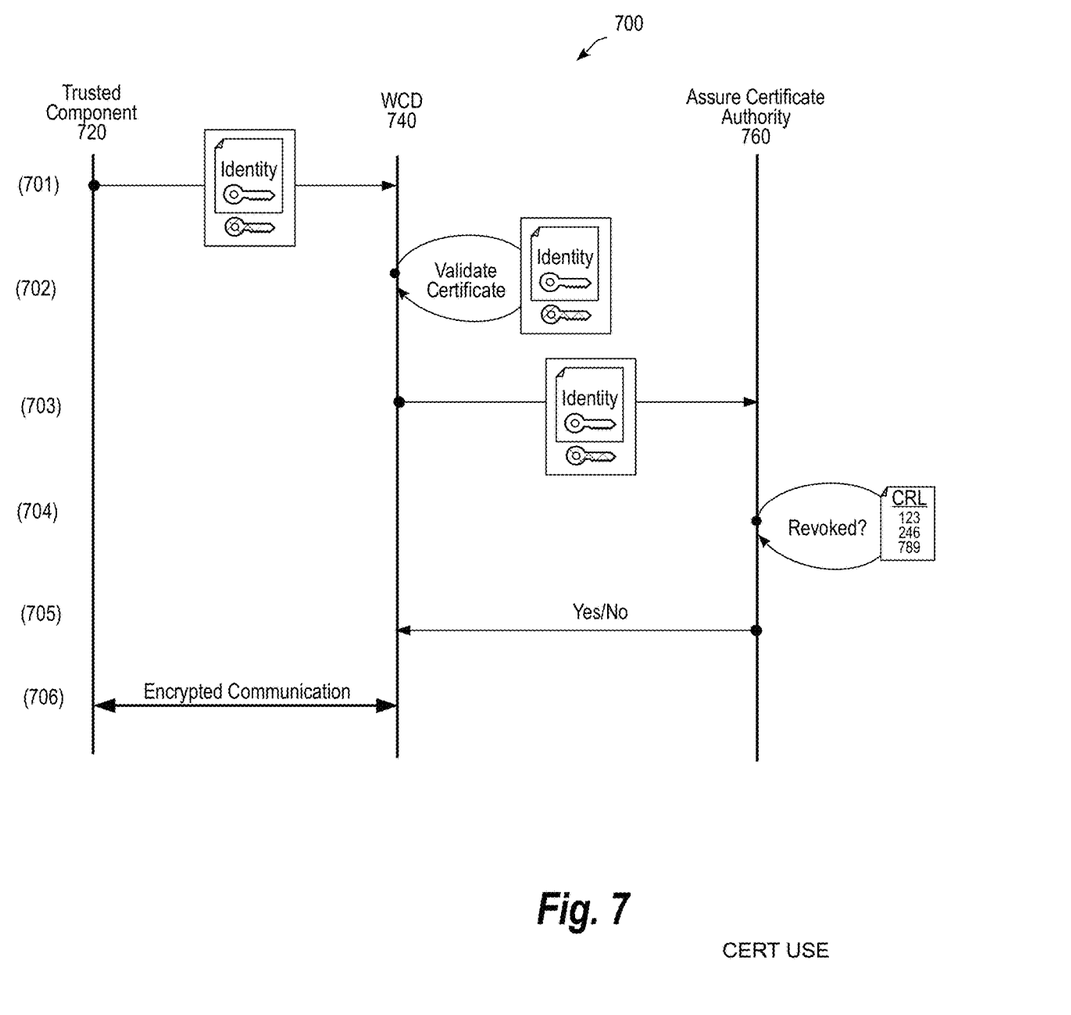
FIG. 7 illustrates a process for using security certificates within a WCD system to ensure trusted communications and proper access between components of the WCD system.

Turning now to FIGS. 6 and 7, the operation of preferred embodiments of the disclosure will be described with reference to the components shown in FIGS. 1 through 5 and described above. Although the following operations are provided for completeness of the disclosure, it will be appreciated that deviations from these operations are envisioned and this description should not be viewed as limiting of the scope of the disclosure.

FIG. 6 is a functional flow diagram generally illustrating a process 600 for creation of a security certificate in accordance with this disclosure. The certificate creation process 600 may be implemented by components of the WCD system 200 illustrated in FIG. 2 and described above. Alternatively, other components may be modified or adapted to implement the several steps discussed here. Reference to components of the same name is for simplicity of discussion only, and the steps may be performed by various components.

The process 600 begins (601) when a trusted component, (Certificate Requestor 620) creates a Certificate Signing Request (CSR) for a "requesting element" (not shown) that desires to communicate with a WCD. As part of that operation, the Certificate Requestor 620 may create a public/private key pair on behalf of the requesting element or the public key may be provided to the Certificate Requestor 620 by the requesting element. The CSR includes information that identifies the requesting element and includes the public key for the requesting element.

Once the CSR is created, the Certificate Requestor 620 transmits (602) the CSR 621 to a component that is responsible for facilitating the creation of security certificates for use in the WCD system. In this example, a CareStation Server 640 is that responsible component. Accordingly, the Certificate Requestor 620 transmits the CSR to the CareStation Server 640. It will be appreciated that, to ensure the CSR is securely delivered to the CareStation Server 640, the Certificate Requestor 640 may first establish a secure connection to the CareStation Server 640 using the Certificate Requestor's own security certificate.

The CareStation Server 640 forwards (603) the CSR to the Assure Certificate Authority 660. In certain embodiments, the CareStation Server 640 may forward additional information along with the CSR 621. For example, the CareStation Server 640 may maintain records about what components are authorized to perform which functions on or in conjunction with a WCD. In such an embodiment, the CareStation Server 640 may forward permission information along with the CSR to the Assure Certificate Authority 660.

The Assure Certificate Authority 660 is configured to perform operations to validate (604) the accuracy of information contained within the CSR 621. For example, the Assure Certificate Authority 660 may have access to records or data that can establish that the CSR 621 did in fact originate with the requesting element and properly names the requesting element. Still further, the Certificate Authority 660 may have access to records or data that confirm the requesting element is authorized access to other components within the WCD system, such as the WCD itself. Even further, the Assure Certificate Authority 660 may have information that either confirms permission information provided by the CareStation Server 640 (if such information was provided) or describes appropriate permissions for the requesting element in the first instance.

If the CSR survives validation, then the Assure Certificate Authority 660 creates a security certificate including the information from the CSR and signs that security certificate using the private key of the Assure Certificate Authority 660. By signing the certificate, the Assure Certificate Authority is both securing the information within the certificate against tampering and attesting to the validity of that information.

With the security certificate signed, the Assure Certificate Authority and CareStation Server 640 return the signed certificate to the Certificate Requestor 620, which then installs the security certificate 650 on the requesting element. In that way, the requesting element (e.g., the Tablet component 203) may now authenticate itself to and have secure communications with the WCD 201, for example.

FIG. 7 illustrates a process 700 for using security certificates within a WCD system to ensure trusted communications and proper access between components of the WCD system. The certificate use process 700 may be implemented by components of the WCD system 200 illustrated in FIG. 2 and described above. Alternatively, other components may be modified or adapted to implement the several steps discussed here. Reference to components of the same name is for simplicity of discussion only, and the steps may be performed by various components.

The process 700 begins (701) when a trusted component 720 desires to initiate communications with another component within a WCD system. The other component is a WCD 740 in this example, but it could be any other component within the WCD system. In accordance with the disclosure, the trusted component 720 initiates a handshake with the WCD 740 to exchange security certificates. During this process, the trusted component 720 sends its security certificate 721 to the WCD 740, and the WCD 740 may return its own security certificate (not shown).

With the security certificate 721 in hand, the WCD 740 performs steps (702) to validate the security certificate 721. For instance, the WCD 740 may identify the Certificate Authority from information within the security certificate 721 to determine if the security certificate 721 is attested to by a trusted Certificate Authority. Once identified, the WCD 740 checks a certificate store (e.g., certificate store 321) to determine if the identified Certificate Authority is trusted by the WCD 740. If so, the WCD 740 uses a stored security certificate (the CA Certificate) to verify the integrity of the received security certificate 721. In short, the WCD 740 uses the CA Certificate to verify the authenticity of the security certificate 721 and that its contents have not been tampered with. The WCD 740 also ensures that the security certificate 721 is within the proper timeframe for its use (e.g., it is currently in effect and has not yet expired).

In an optional step (703), the WCD 740 (or other receiving component) may perform a check to ensure that the security certificate 721 has not been revoked since it was issued. In one embodiment, the WCD 740 transmits the security certificate 721 (or a portion thereof, such as the serial number) to another component, such as the Assure Certificate Authority 760, for verification.

In such an embodiment, the Assure Certificate Authority 760 would compare (704) the received security certificate 721 against a Certificate Revocation List (CRL) to determine if the security certificate 721 has been revoked. The Assure Certificate Authority 760 would then return (705) a pass/fail or yes/no response to indicate whether the security certificate had been revoked.

In an alternative embodiment, rather than transmit the security certificate, the WCD 740 may request (703) the CRL from the Assure Certificate Authority 760, which would then return (705 the CRL to the WCD 740 so that the WCD 740 can itself determine if the security certificate has been revoked. In such an embodiment, the WCD 740 could cache the CRL for future use to reduce the number of network communications it performs for the purpose of certificate verification.

If the security certificate 721 is adequately verified and confirmed, the WCD 740 may then allow a communication session (706) with the trusted component 720. In addition, through the exchange of security certificates and, hence, public keys, the communication session may be encrypted between the two components to ensure that the data exchanged is not compromised. However, if the security certificate 721 fails any of the tests, the WCD 740 prohibits communication with the trusted component 720 (which now becomes untrusted). In various embodiments, when the WCD 740 initiates the secure connection, it may use the security certificate 721, and specifically permission fields, to determine which operations the trusted component 720 is allowed to perform. Although referred to generically as a permission field, it will be appreciated that the WCD 740 may use any data within the security certificate (such as an "element type" field) to control the extent of permission that is granted to the trusted component 720. In other words, the security certificate 72 may, but need not have a dedicated field that explicitly describes permissions. Operative permissions may be implied based on other data within the security certificate. For example, the security certificate may contains a device type field that describes the type of connecting element, such as Tablet, Assistant, Manufacturing System, etc., and various permissions my be assigned to different device types. Another example is a region field that describes the geographical region for the trusted component, such as United States, European Union, Canada, Japan, etc.

Patient Data Association, Security and Privacy

In various embodiments, most elements of the WCD System transfer and/or store protected patient data. In practice, it is important that only users authorized to view protected patient data are able to do so. Accordingly, embodiments of the disclosure provide several methods to ensure this feature. For example, data connections among networked elements use security certificates for authentication and authorization, as described above. In addition, data transfers between trusted components are encrypted. Patient data transmissions may include an identifier (UID) that uniquely associates the transmitted data with the patient and WCD device in use.

Figure 8:
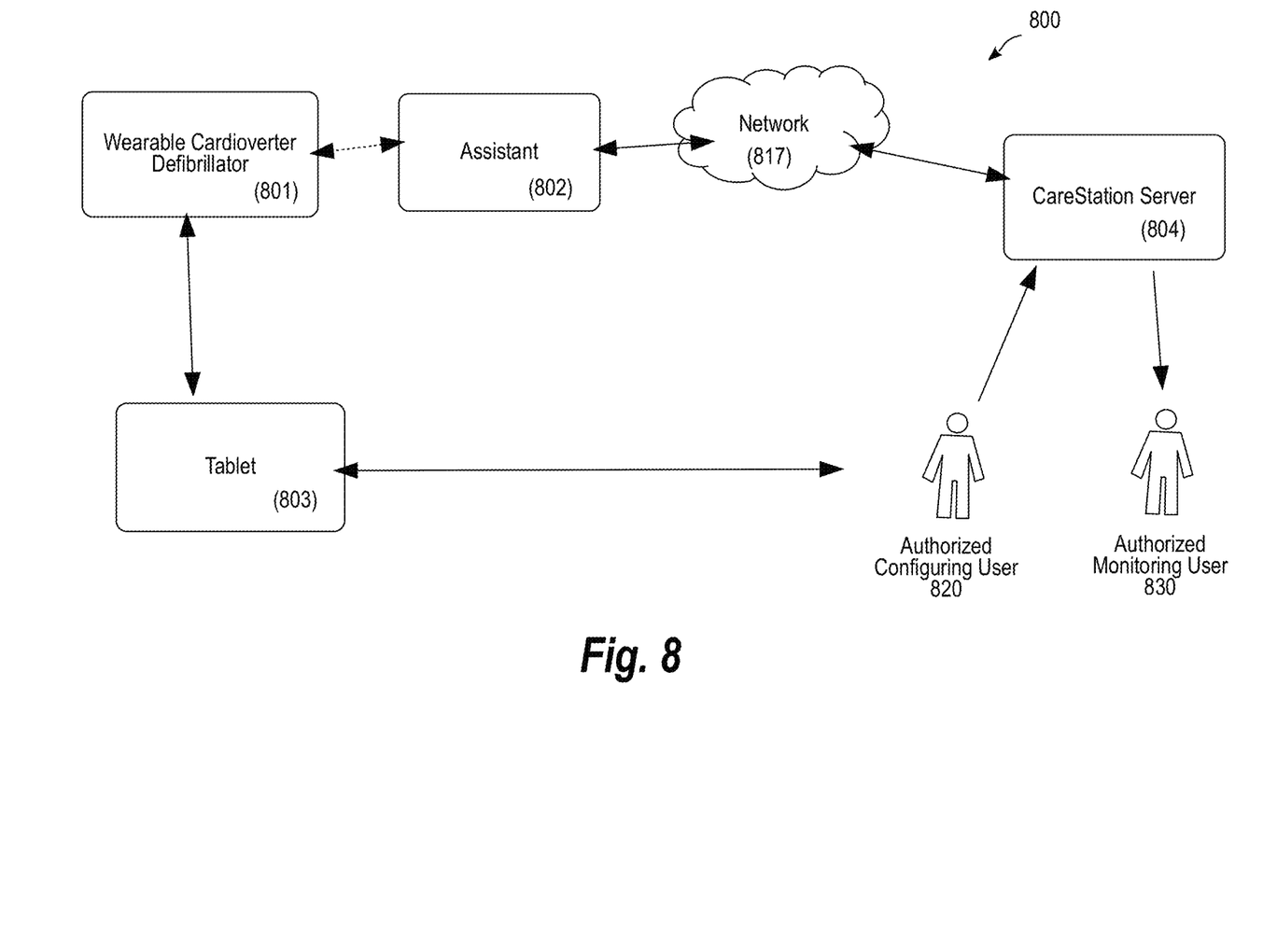
FIG. 8 illustrates an embodiment that implements a patient unique identifier (UID) and the process for its use in the WCD System.

FIG. 8 illustrates an embodiment that implements a patient unique identifier (UID) and the process for its use in the WCD System 800. As illustrated in FIG. 8, when a trusted component (e.g., Tablet 803) creates a 'new patient' on the WCD 801, the WCD 801 clears any existing patient data on the device and establishes a new UID for the new patient. The WCD 801 may then retain that new UID until another component, either Tablet 803 or perhaps a different component, performs the next 'new patient' operation.

A user authorized to view a patient's data and to configure CareStation data 804 obtains the UID for that patient/WCD assignment. That user then becomes the Authorized Configuring User 820.

The Authorized Configuring User 820 activates monitoring of the associated patient on the CareStation Server 804 using the UID. This operation uniquely associates data that the CareStation Server 804 receives for that UID with the associated patient. In the preferred embodiment, any UID can be used only once, which limits patient data access to a set of authorized users as determined by CareStation configuration.

The WCD 801 may periodically send patient data to the Assistant 802, or it may send the data upon request. Either way, the WCD 801 includes the UID as part of the transmission.

The Assistant 802 in turn sends the patient data to the CareStation Server 804, which stores it in association with the received UID. Any Authorized Monitoring User(s) 830 access the patient data on the CareStation Server 804, which uses the Patient/UID association established above. In this way, only authorized users have access to the particular patient data.

Benefits of the Disclosed Embodiments

The disclosed embodiments provide a number of benefits over existing technologies. For example, various embodiments provide a private, unique and highly secure authentication mechanism for allowing communication access to a medical device using standard network technologies and protocols. This is accomplished in some embodiments by using special security certificates issued by a dedicated and separate certificate authority and a system to generate, manage, validate, and use them.

Various embodiments provide a private, unique and highly secure mechanism to control authorized operations on a medical device over standard network technologies and protocols.

In some embodiments, security certificates are managed using a 'cloud' based and dedicated certificate authority and certificate management system, allowing elements of the distributed system to use certificate related services using standard communication technologies and protocols in a wide variety of locations.

These and other benefits will become apparent to those skilled in the art from a study of the teachings of this disclosure, and from reasonable experimentation with various embodiments.

Embodiments provide a unique and reliable mechanism to associate clinical and personal data collected on a medical device with a unique patient data in other elements of a distributed system. These embodiments provide access control to ensure security and privacy of protected patient data on all elements of the system.

In this description, numerous details have been set forth in order to provide a thorough understanding of the described embodiments. In other instances, well-known features have not been described in detail in order to not obscure unnecessarily the description.

A person skilled in the art in view of this description will be able to practice the present invention, which is to be taken as a whole. The specific embodiments disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

What is claimed is:

1. A patient monitoring medical device system, comprising:
a trusted component intended for communication with a patient monitoring medical device, the patient monitoring medical device comprising a wearable cardiac monitoring system, the trusted component including:
a processor configured to execute instructions;
a communication component configured to facilitate communication between the trusted component and other components; and
a memory including a certificate store in which is stored:
a security certificate, the security certificate including:
information that specifically identifies the trusted component,
a public key that enables encryption of data intended to be delivered to the trusted component,
at least one data field that implies at least one function that the trusted component may perform in connection with the patient monitoring medical device wherein the at least one data field comprises an element type, and further wherein the element type has an associated set of permissions that authorize a set of tasks that the trusted component may perform in connection with the patient monitoring medical device system, and
a signature that authenticates the security certificate as being attested to by a Certificate Authority; and
a private key corresponding to the public key;
wherein the processor is programmed to cause the communication component to transmit the security certificate to the patient monitoring medical device in support of a request for communication with the patient monitoring medical device.

2. The patient monitoring medical device system recited in claim 1, wherein the Certificate Authority is a component of the patient monitoring medical device system.

3. The patient monitoring medical device system recited in claim 1, wherein the wearable cardiac monitoring system comprises a Wearable Cardioverter Defibrillator.

4. The patient monitoring medical device system recited in claim 3, wherein the wearable cardioverter defibrillator is further configured to deny secure communications with the trusted component if the security certificate is not properly attested to by the Certificate Authority.

5. The patient monitoring medical device system recited in claim 4, wherein the wearable cardioverter defibrillator is further configured to deny secure communications with the trusted component if the security certificate is revoked.

6. The patient monitoring medical device system recited in claim 1, wherein the patient monitoring medical device is further configured to deny secure communications with the trusted component if the security certificate is not properly attested to by the Certificate Authority.

7. The patient monitoring medical device system recited in claim 1, wherein the patient monitoring medical device is further configured to deny secure communications with the trusted component if the security certificate is revoked.

8. The patient monitoring medical device system recited in claim 1, wherein the trusted component is further configured to communicate data from the patient monitoring medical device to a cloud-based server.

9. The patient monitoring medical device system recited in claim 1, wherein the secure communication includes patient physiological data that can be used in treating a medical condition.

* * * * *